(12) United States Patent
Benner et al.

(10) Patent No.: US 9,725,713 B1
(45) Date of Patent: Aug. 8, 2017

(54) IN VITRO SELECTION WITH EXPANDED GENETIC ALPHABETS

(71) Applicants: Steven A Benner, Gainesville, FL (US); Zunyi Yang, Gainesville, FL (US)

(72) Inventors: Steven A Benner, Gainesville, FL (US); Zunyi Yang, Gainesville, FL (US)

(*) Notice: Subject to any disclaimer, the term of this patent is extended or adjusted under 35 U.S.C. 154(b) by 207 days.

(21) Appl. No.: 14/082,800

(22) Filed: Nov. 18, 2013

Related U.S. Application Data

(63) Continuation-in-part of application No. 13/493,172, filed on Jun. 11, 2012, now Pat. No. 8,586,303, which is a continuation-in-part of application No. 12/999,138, filed on Dec. 15, 2010, now Pat. No. 8,614,072, which is a continuation-in-part of application No. 11/656,317, filed on Jan. 22, 2007, now abandoned, which is a continuation-in-part of application No. 12/800,826, filed on Jan. 22, 2007, now abandoned.

(51) Int. Cl.
*C12Q 1/68* (2006.01)
*C12N 15/10* (2006.01)

(52) U.S. Cl.
CPC .................. *C12N 15/1048* (2013.01)

(58) Field of Classification Search
CPC ................................. C12N 15/1048
USPC .................................. 435/6.1, 91.1
See application file for complete search history.

(56) References Cited

U.S. PATENT DOCUMENTS

| | | |
|---|---|---|
| 5,965,363 A | 10/1999 | Monforte et al. |
| 6,569,620 B1 | 5/2003 | Gold et al. |
| 6,613,526 B2 | 9/2003 | Heilig |
| 6,706,482 B2 | 3/2004 | Smith |
| 6,716,580 B2 | 4/2004 | Gold et al. |
| 6,716,583 B2 | 4/2004 | Gold |
| 6,730,482 B2 | 5/2004 | Gold et al. |
| 6,855,496 B2 | 2/2005 | Pagratis et al. |
| 6,933,116 B2 | 8/2005 | Gold |
| 7,176,295 B2 | 2/2007 | Biesecker et al. |
| 7,368,236 B2 | 5/2008 | Gold |
| 7,629,151 B2 | 12/2009 | Gold et al. |
| 7,709,192 B2 | 5/2010 | Gold |
| 7,947,447 B2 | 5/2011 | Zichi et al. |
| 7,964,356 B2 | 6/2011 | Zichi et al. |
| 8,071,737 B2 | 12/2011 | Gold |

(Continued)

*Primary Examiner* — Jezia Riley

(57) ABSTRACT

This invention provides for products and processes for binding to a preselected target, where the process involves contacting this target to an oligonucleotide molecule that contains one or more "non-standard" nucleotides, which are nucleotide analogs that, when incorporated into oligonucleotides (DNA or RNA, collectively xNA), present to a complementary strand in a Watson-Crick pairing geometry a pattern of hydrogen bonds that is different from the pattern presented by adenine, guanine, cytosine, and uracil. This disclosure provides an example where such an oligonucleotide molecule contains a single 2-amino-8-(1'-β-D-2'-deoxyribofuranosyl)-imidazo[1,2-a]-1,3,5-triazin-4(8H)one and a single 6-amino-5-nitro-3-(1'-β-D-2'-deoxyribofuranosyl)-2(1H)-pyridone, and where the target is a cell, and is obtained by a process of in vitro selection.

12 Claims, 1 Drawing Sheet

(56) References Cited

U.S. PATENT DOCUMENTS

2004/0106108 A1* 6/2004 Grenier ............... C12Q 1/6823
435/6.18

* cited by examiner pyAAD
Acceptor
Acceptor
Donor
pyAAD
Acceptor
Acceptor
Donor
pyDDA
Donor
Donor
Acceptor
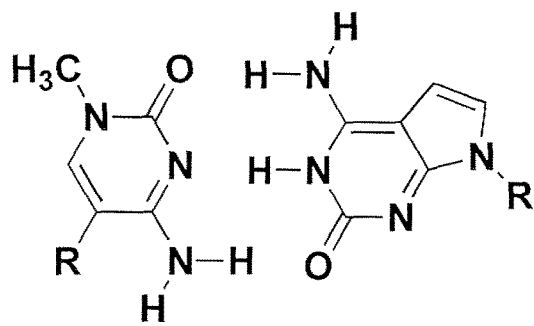
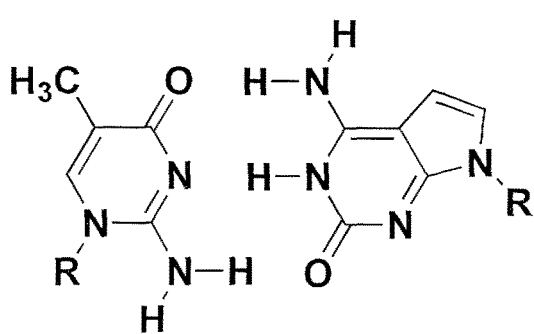
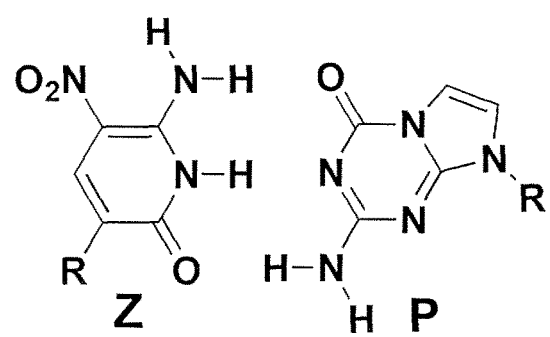
puDDA
Donor
Donor
Acceptor
puDDA
Donor
Donor
Acceptor
puAAD
Acceptor
Acceptor
Donor

SEQUENCE LISTING

<160> NUMBER OF SEQ ID NOS: 16

<210> SEQ ID NO 1
<211> LENGTH: 52
<212> TYPE: DNA

```
<213> ORGANISM: Artificial Sequence
<220> FEATURE:
<221> NAME/KEY: misc_feature
<222> LOCATION: (17)..(36)
<223> OTHER INFORMATION: n=a, g, c, t, z or p phosphoramidite
<220> FEATURE:
<223> OTHER INFORMATION: Synthetic

<400> SEQUENCE: 1
tcccgagtga cgcagcnnnn nnnnnnnnn nnnnnnggac acggtggctg ac         52

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
tcccgagtga cgcagc                                                16

<210> SEQ ID NO 3
<211> LENGTH: 16
<212> TYPE: DNA
<213> ORGANISM: Artificial Sequence
<220> FEATURE:
<223> OTHER INFORMATION: Synthetic

<400> SEQUENCE: 3
gtcagccacc gtgtcc                                                16

<210> SEQ ID NO 4
<211> LENGTH: 56
<212> TYPE: DNA
<213> ORGANISM: Artificial Sequence
<220> FEATURE:
<223> OTHER INFORMATION: Synthetic

<400> SEQUENCE: 4
ccatctcatc cctgcgtgtc tccgactcag gatgattgcc tcccgagtga cgcagc    56

<210> SEQ ID NO 5
<211> LENGTH: 56
<212> TYPE: DNA
<213> ORGANISM: Artificial Sequence
<220> FEATURE:
<223> OTHER INFORMATION: Synthetic

<400> SEQUENCE: 5
ccatctcatc cctgcgtgtc tccgactcag gacattactt tcccgagtga cgcagc    56

<210> SEQ ID NO 6
<211> LENGTH: 39
<212> TYPE: DNA
<213> ORGANISM: Artificial Sequence
<220> FEATURE:
<223> OTHER INFORMATION: Synthetic

<400> SEQUENCE: 6
cctctctatg ggcagtcggt gatgtcagcc accgtgtcc                       39

<210> SEQ ID NO 7
<211> LENGTH: 52
<212> TYPE: DNA
<213> ORGANISM: Artificial Sequence
<220> FEATURE:
<221> NAME/KEY: misc_feature
```

<222> LOCATION: (23)..(23)
<223> OTHER INFORMATION: n = z, non-standard nucleotide of the invention
<220> FEATURE:
<221> NAME/KEY: misc_feature
<222> LOCATION: (30)..(30)
<223> OTHER INFORMATION: n = p, non-standard nucleotide of the invention
<220> FEATURE:
<223> OTHER INFORMATION: Synthetic

<400> SEQUENCE: 7
tcccgagtga cgcagccccc ggngggattn atcggtggac acggtggctg ac            52

<210> SEQ ID NO 8
<211> LENGTH: 52
<212> TYPE: DNA
<213> ORGANISM: Artificial Sequence
<220> FEATURE:
<221> NAME/KEY: misc_feature
<222> LOCATION: (23)..(23)
<223> OTHER INFORMATION: n = z, non-standard nucleotide of the invention
<220> FEATURE:
<223> OTHER INFORMATION: Synthetic

<400> SEQUENCE: 8
tcccgagtga cgcagccccc ggngggattg atcggtggac acggtggctg ac            52

<210> SEQ ID NO 9
<211> LENGTH: 52
<212> TYPE: DNA
<213> ORGANISM: Artificial Sequence
<220> FEATURE:
<221> NAME/KEY: misc_feature
<222> LOCATION: (23)..(23)
<223> OTHER INFORMATION: n = z, non-standard nucleotide of the invention
<220> FEATURE:
<223> OTHER INFORMATION: Synthetic

<400> SEQUENCE: 9
tcccgagtga cgcagccccc ggngggatta atcggtggac acggtggctg ac            52

<210> SEQ ID NO 10
<211> LENGTH: 52
<212> TYPE: DNA
<213> ORGANISM: Artificial Sequence
<220> FEATURE:
<221> NAME/KEY: misc_feature
<222> LOCATION: (30)..(30)
<223> OTHER INFORMATION: n = p, non-standard nucleotide of the invention
<220> FEATURE:
<223> OTHER INFORMATION: Synthetic

<400> SEQUENCE: 10
tcccgagtga cgcagccccc ggcgggattn atcggtggac acggtggctg ac            52

<210> SEQ ID NO 11
<211> LENGTH: 52
<212> TYPE: DNA
<213> ORGANISM: Artificial Sequence
<220> FEATURE:
<221> NAME/KEY: misc_feature
<222> LOCATION: (30)..(30)
<223> OTHER INFORMATION: n = p, non-standard nucleotide of the invention
<220> FEATURE:
<223> OTHER INFORMATION: Synthetic

<400> SEQUENCE: 11
tcccgagtga cgcagccccc ggtgggattn atcggtggac acggtggctg ac    52

<210> SEQ ID NO 12
<211> LENGTH: 52
<212> TYPE: DNA
<213> ORGANISM: Artificial Sequence
<220> FEATURE:
<223> OTHER INFORMATION: Synthetic

<400> SEQUENCE: 12
tcccgagtga cgcagccccc ggcgggattg atcggtggac acggtggctg ac    52

<210> SEQ ID NO 13
<211> LENGTH: 52
<212> TYPE: DNA
<213> ORGANISM: Artificial Sequence
<220> FEATURE:
<223> OTHER INFORMATION: Synthetic

<400> SEQUENCE: 13
tcccgagtga cgcagccccc ggtgggatta atcggtggac acggtggctg ac    52

<210> SEQ ID NO 14
<211> LENGTH: 52
<212> TYPE: DNA
<213> ORGANISM: Artificial Sequence
<220> FEATURE:
<223> OTHER INFORMATION: Synthetic

<400> SEQUENCE: 14
tcccgagtga cgcagccccc ggcgggatta atcggtggac acggtggctg ac    52

<210> SEQ ID NO 15
<211> LENGTH: 52
<212> TYPE: DNA
<213> ORGANISM: Artificial Sequence
<220> FEATURE:
<223> OTHER INFORMATION: Synthetic

<400> SEQUENCE: 15
tcccgagtga cgcagccccc ggtgggattg atcggtggac acggtggctg ac    52

<210> SEQ ID NO 16
<211> LENGTH: 52
<212> TYPE: DNA
<213> ORGANISM: Artificial Sequence
<220> FEATURE:
<221> NAME/KEY: misc_feature
<222> LOCATION: (23)..(23)
<223> OTHER INFORMATION: n = z, non-standard nucleotide of the invention
<220> FEATURE:
<221> NAME/KEY: misc_feature
<222> LOCATION: (30)..(30)
<223> OTHER INFORMATION: n = p, non-standard nucleotide of the invention
<220> FEATURE:
<223> OTHER INFORMATION: Synthetic

<400> SEQUENCE: 16
tcccgagtga cgcagccccc ggngggattn atcggtggac acggtggctg ac    52

IN VITRO SELECTION WITH EXPANDED GENETIC ALPHABETS

CROSS REFERENCE TO RELATED APPLICATIONS

This application is a continuation-in-part of the U.S. patent application having a Ser. No. 13/493172, having the title "In vitro selection with expanded genetic alphabets", and which was filed on Jun. 11, 2012, and which is co-pending. U.S. patent application having a Ser. No. 13/493172 is a continuation in part of U.S. patent application Ser. No. 12/999138, filed Dec. 15, 2010 having the title "Polymerase incorporation of non-standard nucleotides". This application is also a continuation-in-part of the U.S. patent application Ser. No. 11/656317, filed Jan. 22, 2007 having the title "DNA containing non-standard nucleosides and their precursors", which is abandoned. This application is also a continuation-in-part of the U.S. patent application Ser. No. 12/800826, filed May 24, 2010 having the title "Non-standard nucleobases implementing the isoguanosine hydrogen bonding patterns", which is abandoned.

STATEMENT OF RIGHTS TO INVENTIONS MADE UNDER FEDERALLY-SPONSORED RESEARCH

This invention was made with government support under HDTRA1-08-1-0052 awarded by the Defense Threat Reduction Agency. The government has certain rights in the invention.

NAMES OF THE PARTIES TO A JOINT RESEARCH AGREEMENT

Not applicable.

INCORPORATION-BY-REFERENCE OF MATERIAL SUBMITTED ON A DISC

None.

BACKGROUND OF THE INVENTION (1) Field of Invention

This invention relates to the field of nucleic acid chemistry, more specifically to nucleotide analogs, and still more specifically to "non-standard" nucleotide analogs that, when incorporated into oligonucleotides (DNA or RNA, collectively xNA), present to a complementary strand in a Watson-Crick pairing geometry a pattern of hydrogen bonds that is different from the pattern presented by adenine, guanine, cytosine, and uracil. Most specifically, this invention combines inventive steps that enable the preparation of function oligonucleotides containing non-standard nucleotides that bind to target molecules (called "aptamers") or catalyze reactions (called "xNAzymes") by a process of "in vitro selection" (or IVS). IVS is sometimes also called "SELEX". Most specifically, this invention claims processes that comprise the creation of xNA libraries, selecting from those libraries individual xNA molecules that perform the preselected function to generate a fraction of xNA molecules having enhanced performance capabilities, PCR amplifying these with less than 5% loss of the non-standard nucleotide, and determining the sequence of certain of those performing molecules (2) Description of Related Art For two decades, many have sought processes that mimic, in the laboratory, biological evolution to select or evolve DNA or RNA (collectively xNA) molecules that act as ligands, receptors, or catalysts. This process has been called Systematic Evolution of Ligands by Exponential Enrichment (SELEX), "in vitro selection", or in vitro evolution (collectively referred to as IVS). The xNA ligands and receptors that bind to a preselected target are called aptamers. xNA molecules that catalyze a preselected reaction are called xNAzymes.

The literature describing the history of development of IVS is summarized in the U.S. patent application having a Ser. No. 13/493172 and the title "In vitro selection with expanded genetic alphabets", which was filed on Jun. 11, 2012, of which this application is a continuation-in-part, and which is incorporated in its entirety by reference.

As generally practiced, IVS generates aptamers or xNAzymes by the following steps:

(a) A library of nucleic acid (xNA) molecules (typically $10^{14}$ to $10^{14}$ different species) is obtained.

(b) The library is then fractionated to create a fraction that contains molecules better able bind to the preselected target(s), or catalyze the preselected reaction(s), than molecules in the fractions left behind. For example, to generate aptamers, this separation can be done by contacting the library with a solid support carrying the target, washing from the support xNA molecules that do not bind, and recovering from the support xNA molecules that have bound. xNA molecules within the library that bind to the target are said to survive the selection.

(c) The surviving xNAs are then used as templates for the polymerase chain reaction (PCR) process. A low level of mutation may be included in the PCR amplification, creating Darwinian "variation" in an in vitro evolution process.

(d) While it is conceivable that aptamers/xNAzymes having useful binding/catalytic power may emerge in the first "round" of selection, they generally do not. When they do not, the cycle is repeated. With each cycle of fractionation/selection and PCR amplification, the resulting fraction of xNA molecules becomes more enriched in those that bind to the preselected target or catalyze the preselected reaction.

(e) The product xNA aptamer(s) and xNAzyme(s) might be useful if their sequences are not known. However, the utility of these products is nearly always enhanced if their sequences are known, as this allows them to be generated separately. To obtain those sequences, standard IVS procedures generally clone the xNA products in their DNA form (either directly for DNA products, or after conversion to a DNA sequence using reverse transcriptase for RNA products) followed by classical sequencing. Alternatively, next generation sequence can be applied to the mixture of survivors. The elements of this approach are reviewed in U.S. Ser. No. 13/493172.

U.S. Ser. No. 13/493172 also summarizes the many advantages that were anticipated when xNA molecules replace protein molecules have also been realized. U.S. Ser. No. 13/493172 also summarizes the disadvantages of IVS technology, where the outcome has often been disappointing.

In retrospect, this disappointing outcome might be viewed as unsurprising. Proteins are built from 20 different amino acid building blocks that carry much chemical functionality, including positively charged nitrogens on lysine and arginine, general acid-base functionality on histidine, hydrophobic groups on leucine and others, polarizable binding groups (as on tryptophan and methionine), metal coordinating groups (cysteine, histidine, and others), and so on. Structural biology and mechanistic biochemistry identifies roles for all of these in the binding between proteins and their ligands. In contrast, nucleic acids carry little of this functionality.

Further, with only four building blocks, nucleic acids have fewer motifs for folding than proteins. For example, a G-rich region might lead to a particular "G-quartet", desired to form a specific binding site for a particular target. However, this quartet might be in equilibrium with an alternative folding motif based on G's elsewhere in a sequence involving G:C pairing. The alternative fold need not have any affinity for a target. There are only a limited numbers of interaction types that can be achieved in DNA with just four letters. Further, with low information density arising from four different building blocks, it is difficult to obtain unambiguous folds from standard xNAs. Further, even if the desired fold is the thermodynamic minimum, it can be kinetically slow to achieve, again because of the low information density in standard xNA.

U.S. Ser. No. 13/493172 also reviews the many attempts to improve IVS with functionalized natural DNA and RNA. However, simply functionalizing standard xNA nucleotides (as in SOMAmers) does not greatly expand its diversity of folds. Nor does it increase the information density of the biopolymer. Further, functionalizing GACT encounters a new set of problems. For example, an xNA molecule having a fluorescent group attached to each nucleobase are hard to make using xNA polymerases. Further, in ways that are not fully understood, having each nucleobase carry a functional group can cause the DNA to cease to follow "rule based" molecular recognition essential for its genetic roles.

U.S. Ser. No. 13/493172 also noted how disadvantages of standard IVS might be mitigated by expanding the number of nucleotides in DNA. For example, rearranging hydrogen bond donor and acceptor groups on the nucleobases increases the number of independently replicable nucleosides in DNA and RNA from four to twelve (FIG. 1). In this "artificially expanded genetic information system" (AEGIS), 12 different nucleotide "letters" pair via six distinguishable hydrogen bonding patterns to give a system that can, in principle, pair, be copied, and evolve like natural DNA, but with higher information density and more functional group diversity.

The potential for using AEGIS to support IVS has been recognized since the proposal of the first AEGIS. Indeed, processes for doing IVS with certain AEGIS-containing nucleotides were claimed by U.S. Pat. No. 5,965,363. However, efforts to implement the process disclosed in that patent have failed. Steps (a) and (b) (above) in the IVS process were possible. Libraries of xNA molecules containing AEGIS components could be prepared, Step (a), and these libraries could be fractionated (Step (b)). However, as discussed in U.S. Ser. No. 13/493172, polymerases were not available to perform PCR on DNA molecules containing multiple AEGIS nucleotides. Further, even after polymerases that copied AEGIS nucleotides were obtained, repeated PCR cycling saw their loss, by perhaps as much as 5% loss per cycle seen when isoguanosine was used to implement the puDDA hydrogen bonding pattern. Efforts to prevent their loss led to DNA molecules with multiple sulfur atoms, undesirable for many applications. Still other AEGIS components suffered epimerization, which prevented their being routinely copied.

Further, even if components in a library of AEGIS-containing oligonucleotides could be amplified and the AEGIS components retained, no downstream tools were available to clone the AEGIS-containing xNA aptamers or xNAzymes. Bacteria were not known to accept AEGIS components Further, no process was available to sequence AEGIS-containing xNA aptamers. After many years of attempting to do IVS based on libraries of AEGIS-containing oligonucleotides, it is clear that any claims covering an AEGIS-based IVS in the prior art were not enabled. This specifically includes the process claimed by U.S. Pat. No. 5,965,363. complement "standard base pairs". Other hydrogen bonding patterns are said to be "non-standard", and to form with their appropriate complement "non-standard base pairs".

Relevant Prior Art

IVS processes with nucleotides that implement standard hydrogen bonding patterns have been known for many decades (see references above). From this art, those of ordinary skill might also be able to perform several of the steps of an IVS process for DNA that contains non-standard nucleotides as well, specifically:

(a) The art does teach an ordinarily skilled artisan how to obtain a library of nucleic acid (xNA) molecules incorporating nucleotides carrying various non-standard nucleobases, such as Z, P, 5-methyl-isoC, isoG, and various analogs of isoG, including B. Phosphoramidites suitably protected to support solid phase synthesis of these are known in the art (see U.S. Ser. No. 13/493172). Several are commercially available. Solid phase synthesis of libraries of DNA molecules is likewise known, involving the use of mixtures of phosphoramidites or split-and-pool synthesis. Libraries of RNA molecules can be obtained by transcribing libraries of encoding DNA molecules.

(b) The art does teach an ordinarily skilled artisan how to fractionate the library to separate molecules that bind preselected target(s), or catalyze preselected reaction(s), from molecules that do not. Fractionation for IVS with non-standard nucleotides is not materially different from that used in standard IVS. Further, a variety of variants of selection processes, and various applications of the derived species have been covered by various patents, including:

U.S. Pat. No. 8,071,737: Nucleic acid ligand complexes. This invention covers a method for preparing a therapeutic or diagnostic complex comprised of a nucleic acid ligand and a lipophilic compound or non-immunogenic, high molecular weight compound U.S. Pat. No. 7,964,356: Method for generating aptamers with improved off-rates. This invention covers methods for producing aptamers and photoaptamers having slower dissociation rate constants than are obtained using SELEX and photoSELEX methods.

U.S. Pat. No. 7,947,447: Method for generating aptamers with improved off-rates. This invention covers improved SELEX methods for producing aptamers that are capable of binding to target molecules and improved photo-SELEX methods for producing photoreactive aptamers.

U.S. Pat. No. 7,709,192: Nucleic acid ligand diagnostic biochip. This invention covers nucleic acid ligand "biochips", consisting of a solid support to which one or more specific nucleic acid ligands is attached in a spatially defined manner.

U.S. Pat. No. 7,629,151: Method and apparatus for the automated generation of nucleic acid ligands. This invention covers a method and device for performing automated SELEX.

U.S. Pat. No. 7,368,236: Methods of producing nucleic acid ligands. This invention covers methods for the identification and production of improved nucleic acid ligands based on the SELEX process.

U.S. Pat. No. 7,176,295: Systematic evolution of ligands by exponential enrichment: blended SELEX. This invention covers a method for generating blended nucleic acid ligands containing non-nucleic acid functional units.

U.S. Pat. No. 6,933,116: Nucleic acid ligand binding site identification. This invention covers a nucleic acid ligand for use as a diagnostic reagent for detecting the presence or absence of a target molecule in a sample, and a diagnostic reagent.

U.S. Pat. No. 6,855,496: Truncation SELEX method. This invention covers a method for identifying nucleic acid ligands by the SELEX method wherein the participation of fixed sequences is eliminated or minimized.

U.S. Pat. No. 6,730,482: Modified SELEX processes without purified protein. This invention covers a method for obtaining nucleic acid ligands against target proteins without directly purifying the target proteins.

U.S. Pat. No. 6,716,583: Methods of producing nucleic acid ligands. This invention covers methods for the identification and production of improved nucleic acid ligands based on the SELEX process.

U.S. Pat. No. 6,716,580: Method for the automated generation of nucleic acid ligands This invention covers a method and device for performing automated SELEX.

U.S. Pat. No. 6,706,482: Conditional-SELEX

This invention covers a method for producing nucleic acid ligands that generate a signal, or cause a decrease in the level of a signal, in the presence of a target molecule U.S. Pat. No. 6,613,526: Systematic evolution of ligands by exponential enrichment: tissue selex This invention covers methods to create high-affinity oligonucleotide ligands to complex tissue targets, specifically nucleic acid ligands having the ability to bind to complex tissue targets, Brief Summary of the Invention This invention provides processes to generate aptamers and xNAzymes that contain nonstandard nucleotide components by in vitro selection (IVS) methods. Specifically, the invention enables steps essential for IVS that have previously not been enabled for xNA molecules containing nonstandard nucleotides: (i) their PCR amplification and (ii) their sequencing. More specifically, this invention generates aptamers and xNAzymes from the nonstandard nucleotides 2-amino-8-(1'-β-D-2'-deoxyribofuranosyl)-imidazo[1,2-a]-1,3,5-triazin-4(8H)one (trivially called dP), 6-amino-5-nitro-3-(1'-β-D-2'-deoxyribofuranosyl)-2(1H)-pyridone (trivially called dZ), and nucleotide analogs carrying the 7-deazaisoguanine (trivially called dB), and isocytosine heterocycles.

BRIEF DESCRIPTION OF THE DRAWINGS

FIG. 1 Watson-Crick pairing rules follow two rules of complementarity: (a) size complementarity (large purines pair with small pyrimidines) and (b) hydrogen bonding complementarity (hydrogen bond donors, D, pair with hydrogen bond acceptors A). Rearranging D and A groups on various heterocycles supports an artificially expanded genetic information system (AEGIS). AEGIS nucleobases can also be functionalized at the position indicated by the "R" in these structures. Thus, AEGIS offers a solution to the limitations of aptamers by increasing the number of building blocks, and functionalizing an expanded set of building blocks.

DESCRIPTION OF INVENTION

Definition Oof Non-Standard Components of an Artificially Expanded Genetic Information System This application teaches a distinction between the hydrogen-bonding pattern (in FIG. 1 nomenclature, pyDAD, for example) and the heterocycle that implements it. Thus, the pyADA hydrogen-bonding pattern is implemented by thymidine, uridine, and pseudouridine. The puDDA hydrogen bonding pattern is implemented by both the heterocycle isoguanosine and 7-deaz-isoguanosine. Heterocycles to implement any particular pre-selected hydrogen-bonding pattern are preferred depending on their chemical properties, for example, high chemical stability or low tautomeric ambiguity. The pyADA, pyDAA, puADD, and puDAD hydrogen bonding patterns are said to be "standard" hydrogen bonding patterns, and to form with their appropriate U.S. Pat. No. 6,569,620: Method for the automated generation of nucleic acid ligands This invention covers a method and device for performing automated SELEX.

Each of these is incorporated in its entirety herein by reference. Each of these could also be applied to IVS based on AEGIS components, if only the steps not enabled in the art were to be enabled.

Processes that are Absent in the Prior Art

Missing from the art for standard IVS and all of its variants, and not obvious to those of ordinary skill in the art, are the remaining steps in the IVS process. Specifically:

(c) Absent from the art prior to the priority date of this application, PCR amplification using AEGIS components is not available. For the instant invention, AEGIS PCR amplification is made available in U.S. patent application Ser. No. 12/999138, having the title: Polymerase incorporation of non-standard nucleotides which is herein incorporated in its entirety by reference, with respect to pyDDA:puAAD pairs. This application provides for processes that PCR amplify DNA containing G, A, C, T, Z, and P nucleotides. AEGIS PCR amplification is made available in U.S. patent application Ser. No. 12/800826, which describes variants of isoguanine with lower amounts of minor tautomeric forms, which is herein incorporated in its entirety by reference, with respect to pyAAD:puDDA pairs.

(d) Also absent in the prior art are processes to do the repeated cycling needed to obtain useful aptamers and DNAzymes for selection survivors containing AEGIS components, as this requires PCR amplification of nucleic acid analogues containing AEGIS components.

(e) Also absent in the prior art are procedures to efficiently sequence DNA containing AEGIS components. While methods in the art, including dideoxy sequencing, might be applied to DNA containing AEGIS components, the challenges associated with this application have to date prevented any successful AEGIS IVS. A workable method of sequencing is disclosed here, and is based on U.S. patent application Ser. No. 12/999138, which is herein incorporated in its entirety by reference. This application provides for processes that convert Z:P pairs in DNA into A:T pairs and/or C:G pairs, or isoC:7-deazaisoG pairs into T:A pairs, enabling a process for efficiently sequencing aptamers/xNAzymes built from G, A, C, T, Z, and P nucleotides. This method for sequencing employs the following steps:

(a) Perform amplification under conditions that convert Z:P pairs sometimes to C:G pairs and sometimes to T:A bases;
(b) Shotgun clone the products of that amplification, now built entirely from standard nucleotides;
(c) Sequence the cloned material using high throughput DNA sequencing; and
(d) Align and compare the sequences recovered.

In this "converting nucleosides" strategy (U.S. Ser. No. 13/493172), two populations of standard DNA are generated from one precursor of GACTZP DNA. Sites that originally held Z in the precursor hold either C or T in the converted sequence. This generates a "C" call half of the time, and a "T" call the other half of the time. Similarly, sites that originally held P will generate either a "G" call or an "A" call. Sites that originally held G, A, C, and T will give uniform calls in all of the sequences returned. Thus, the sequence of the precursor and the positions of Z and P in that sequence can be inferred.

Description of the Preferred Embodiments

The presently preferred AEGIS components to support IVS are nucleosides that implement the pyDDA and puAAD hydrogen bonding patterns are as follows. For DNA, presently preferred implementation of the pyDDA hydrogen bonding pattern is the nucleoside analog 6-amino-5-nitro-3-(1'-β-D-2'-deoxyribofuranosyl)-2(1H)-pyridone. The presently preferred implementation of the puAAD hydrogen bonding pattern is the nucleoside analog (2-amino-8-(1'-β-D-2-deoxyribofuranosyl)-imidazo[1,2-a]-1,3,5-triazin-4 (8H)one. These are trivially named dZ and dP; their ribonucleoside analogues are preferred to implement IVS based on an RNA-like scaffold.

For the pyAAD hydrogen-bonding pattern, the presently preferred nucleobase embodiments are isocytosine and pseudocytosine disclosed in U.S. Pat. No. 7,741,294, which is incorporated in its entirety herein by reference. For the puDDA hydrogen-bonding pattern, the presently preferred nucleobase embodiment is 7-deazaisoguanine.

EXAMPLE

Example 1

Selection of an Aptamer that Binds to a Line of Human Breast Cancer Cells

This in vitro selection (or AEGIS-SELEX) example exploited two additional nucleotides (2-amino-8-(1'-β-D-2-deoxyribofuranosyl)-imidazo[1,2-a]-1,3,5-triazin-4(8H) one, trivially called P, and 6- amino-5-nitro-3-(1'-β-D-2'-deoxyribofuranosyl)-2(1H)-pyridone, trivially called Z).

Synthesis and Purification of GACTZP Libraries Containing Four Natural Nucleotides (G, A, C, and T) and AEGIS Nucleotides (Z and P) to Support AEGIS-SELEX.

All dZ and dP containing oligonucleotides (Tables S1 and S4) were synthesized using standard phosphoramidite chemistry on controlled pore glass supports on an ABI 394 DNA Synthesizer. Protected dZ and dP phosphoramidites were purchased from Firebird Biomolecular Sciences LLC (Alachua, Fla., www.firebirdbio.com, Cat. # DZPhosphor-101, Cat. # DPPhosphor-102). ). Standard phosphoramidites (Bz-dA, Ac-dC, dmf-dG, and dT) were purchased from Glen Research (Sterling, Va.). The oligonucleotides were designed to have forward and reverse primer binding sites (each 16 nucleotides in length) with a random region (20 nts) containing GACTZP (six nucleotides) at each site in equimolar concentrations. Coupling times were 60 seconds. The CPG-bound DMT-off oligonucleotides were incubated with triethylamine-acetonitrile (1:1 v/v, 1.5 mL) for 1 hour at 25° C., followed by removal of supernatant, the CPG-bound oligonucleotides were treated with another 1.5 mL of triethylamine-acetonitrile (1:1 v/v) for overnight at 25° C. After removal of supernatant, the CPG-bound oligonucleotides were incubated with 1.0 mL of DBU in anhydrous $CH_3CN$ (1 M) at room temperature for ~18 hours to remove the protecting groups on dZ. After removal of $CH_3CN$, dZ and dP containing oligonucleotides were retreated with $NH_4OH$ (55° C., overnight). The product mixture was resolved by denaturing PAGE (7 M urea), and extracted with TEAA buffer (0.2 M, pH=7.0). The product was desalted by Sep-Pac® Plus C18 cartridges (Waters). All 5'-biotinylated dZ and dP containing potential aptamers were synthesized, deprotected, and purified in house based on the above methods. All standard 5'-biotinylated oligonucleotides were purchased from IDT and purified by HPLC.

Cell Lines.

Triple negative breast cancer cells (MDA-MB-231, ATCC® HTB-26™) were cultured using ATCC recommended media and reagents (Incubate cultures at 37° C. without $CO_2$. http://atcc.org/Products/All/HTB-26.aspx#7301B7F956944F8382B6192957C08A3B).

Experimental Procedure of AEGIS-SELEX.

To begin the AEGIS-SELEX experiment, MBA-MD-231 cells were seeded in culture flasks (25 mL). These cells adhere to the walls of the flask and grown to about 97% coverage of culture flask. Cells were washed with washing buffer (4.5 g/liter glucose, 5 mM $MgCl_2$ in Dulbecco's PBS). Five nanomoles of GACTZP DNA library was dissolved in 700 µl of binding buffer (4.5 g/liter glucose, 5 mM $MgCl_2$, 0.1 mg/ml tRNA and 1 mg/ml BSA, all in Dulbecco's PBS).

The GACTZP DNA library was denatured by heating at 95° C. for 3 min, and then "snap cooled" on ice for 10 min. The library was then incubated with the cells, still adhering to the walls of the flask at 4° C. on rocker for 1 hour. Cells were thrice gently washed with washing buffer to remove unbound sequences. Binding buffer (0.5 mL) was added and the cells scraped off the plate using cell scraper to recover cell/ DNA complexes.

Once the cells were scraped from the walls of the flask into a suspension in PBS buffer, they were heated (95° C. for 15 min). The resulting mixture centrifuged at 14000 rpm to pellet the cell debris. The supernatant containing the ssDNA survivors were recovered.

The recovered survivors were then amplified by six-nucleotide PCR using FITC- and biotin-labeled primers (Table S1) with six nucleotide triphosphate mixture (dZTP, dPTP, dGTP, dATP, dCTP, and dTTP). Different PCR cycles (from 8 cycles to 25 cycles) were tested to determine the optimum number of cycles for preparative PCR to produce maximal amount of amplicon with less PCR artifacts. Reagents and conditions are listed in Table S2.

TABLE S1

GACTZP DNA library, 6-nucleotide PCR primers, and barcoded primers for deep sequencing

| Name | Sequence |
|---|---|
| GACTZP DNA Library SEQ ID NO. 1 | 5'-TCCCGAGTGACGCAGC-*NNNNNNNNNNNNNNNNNNNN*-GGACACGGTGGCTGAC-3'; *N* = equimolar A, G, C, T, Z, and P phosphoramidites |

TABLE S1-continued

GACTZP DNA library, 6-nucleotide PCR primers, and barcoded primers for deep sequencing

| Name | Sequence |
| --- | --- |
| FITC-Primer SEQ ID NO. 2 | 5'-FITC-TCCCGAGTGACGCAGC-3' |
| Biotin-Primer SEQ ID NO. 3 | 3'-CCTGTGCCACCGACTG-Biotin-5' |
| A_Code2_Forward_56mer SEQ ID NO. 4 | Adaptor A Key Barcode2 Forward Primer 5'-CCATCTCATCCCTGCGTGTCTCCGACTCAG-GATGATTGCC-TCCCGAGTGACGCAGC-3' |
| A_Code6_Forward_56mer SEQ ID NO.5 | Adaptor A Key Barcode6 Forward Primer 5'-CCATCTCATCCCTGCGTGTCTCCGACTCAG-GACATTACTT-TCCCGAGTGACGCAGC-3' |
| trP_Reverse_39mer SEQ ID NO. 6 | Adaptor trP1 Reverse Primer 5'-CCTCTCTATGGGCAGTCGGTGAT-GTCAGCCACCGTGTCC-3' |

TABLE S2

Typical six-nucleotide PCR amplification of GACTZP DNA library:

| Reagents | Volume (μL) | Final conc. |
| --- | --- | --- |
| $H_2O$ | 30.5 | |
| FITC-Primer + Biotin Primer mixture (each 10 μM) | 2.5 | 0.5 μM |
| Six-Nucleotide Mix of 10× | | |
| dA, T, G/TPs (1 mM of each) | 5.0 | 0.1 mM of each |
| dCTP (2 mM) | | 0.2 mM |
| dZTP (1 mM) | | 0.1 mM |
| dPTP (6 mM) | | 0.6 mM |
| 10× ThermoPol Buffer (pH = 8.0) | 5.0 | 1× |
| GACTZP DNA library (survivors) | 5.0 | (10% of reaction volume) |
| HS Takara Taq DNA polymerase (2.5 units/μL) | 2 | 0.10 (U/μL) |
| Total volume (uL) | 50.0 | |

Note:
1 × ThermoPol Reaction Buffer (20 mM Tris-HCl, 10 mM $(NH_4)_2SO_4$, 10 mM KCl, 2 mM $MgSO_4$, 0.1% Tritonx-100, pH 8.0 at 25° C.); PCR cycling conditions: one cycle of 94° C. for 1 min; 8 cycles~25 cycles of (94° C. for 20 s, 55° C. for 30 s, 72° C. for 5 min); 72° C. for 10 min; 4° C. forever.

Upon completion of six-nucleotide PCR, the FITC-labeled DNA stands were separated from the biotinylated strands by affinity purification with streptavidin-coated Sepharose beads (GE Healthcare Bio-Sciences Corp., Piscataway), followed by alkaline denaturation (with NaOH, 50 mM), and neutralized. The surviving ssDNA was desalted and resuspended in binding buffer to a final concentration of 0.5 μM.

The survivors were denatured at 95° C., snap cooled and used to perform the second round of selection using the same procedure as described for the first round of selection. As a proof of concept, no counter selection was designed in the course of the selection. The entire selection process was repeated until a sustained significant enrichment was obtained at $11^{th}$ and $12^{th}$ rounds. During the selection, the stringency of selection was increased by increasing the volume of washing buffer and the number of washes.

Deep Sequencing of GACTZP DNA Survivors Using Next Generation Sequencing Technology.

Sequencing was done following the "conversion" strategy. Solutions containing enriched GACTZP DNA survivors, after 12 rounds of AEGIS-SELEX, were divided into two equal parts. These were separately converted into standard GACT DNA under two conversion conditions using primers that carried barcodes for the Ion Torrent instrument (Table S1):

TABLE S3

Converting Z:P to C:G (barcode 6) or converting Z:P to T:A and C:G (barcode2)

| Components | Z:P to C:G conversion | Z:P to T:A and C:G conversion | Final Conc. |
| --- | --- | --- | --- |
| $ddH_2O$ | 33 μl | 33 μl | 50 μl |
| A_Code6_For_56mer (10μM) | 2 μl | | 0.4 μM |
| trP_ Rev_39mer (10 μM) | 2 μl | | 0.4 μM |
| A_Code2_For_56mer (10 μM) | | 2 μl | 0.4 μM |
| trP_ Rev_39mer (10 μM) | | 2 μl | 0.4 μM |
| 12th-Round Survivors | 1 μl | 1 μl | |
| 10× Five-Nucleotide Mix | | | |
| dZTP (0.1 mM) | 5 μl | | 0.01 mM |
| dC, G/TPs (4 mM of each) | | | 0.4 mM of each |
| dT, A/TPs (0.4 mM) | | | 0.04 mM of each |
| 10× Five-Nucleotide Mix | | | |
| dPTP (2 mM) | | 5 μl | 0.2 mM |
| dC, G/TPs (1 mM of each) | | | 0.1 mM of each |
| dT, A/TPs (1 mM) | | | 0.1 mM of each |
| 10× ThermoPol Buffer (pH 8.8) | 5 μl | 5 μl | 1× |
| JumpStart Taq (2.5 units/μl, Sigma) | 2 μl | 2 μl | 0.1 (U/μl) |

Notes:
1. 1 × ThermoPol Reaction Buffer (20 mM Tris-HCl, 10 mM $(NH_4)_2SO_4$, 10 mM KCl, 2 mM $MgSO_4$, 0.1% Tritonx-100, pH 8.8 at 25° C.);
2. PCR conditions: one cycle of 94° C. for 1 min; 11 cycles of (94° C. for 20 s, 57° C. for 30 s, 72° C. for 90 s); 72° C. for 10 min; 4° C. forever.

Following conversion, the samples were combined, purified by native agarose gel, and submitted to Ion Torrent "NextGen" sequence (University of Florida, ICBR sequencing core facility). The products were aligned to identify sequences derived from a single common aptamer "ancestor", and the ancestral sequence was inferred (see below).

Inference of GACTZP Aptamer Sequences.

Ion Torrent sequencing produced 2,975,012 reads, delivered in FASTQ format. Reads that did not contain exact matches to the barcode, forward priming, and reverse priming sequences were discarded, leaving 1,586,297 reads. To minimize miscalling, any read present in less than 80 copies was removed from the analysis. Remaining reads were then clustered using custom software (Bradley, FfAME), which ignored differing barcodes while clustering, and accepting single-step changes within sequence reads. Clustered sequences were then separated by barcode, with variable sites being compared between each barcode (differentiating the two conversion conditions). Sites where variation resembled previously documented base percentages (the first condition with barcode6 generate predominately Z:P to C:G conversion, or the second condition with barcode2 produce Z:P to C:G and T:A, ~50% of each conversion) in each conversion protocol were marked as likely locations of conversion and were assigned as dZ and dP in the common "ancestor".

TABLE S4

Re-synthesis and purification of the dominant aptamer ZAP-2012 and variants.

| Name | Sequence |
|---|---|
| ZAP-2012 (Z23-P30) SEQ ID NO. 7 | 5'-Biotin-TCCCGAGTGACGCAGC-CCCCGGZGGGATTPATCGGT-GGACACGGTGGCTGAC-3' |
| Z23-G30 SEQ ID NO. 8 | 5'-Biotin-TCCCGAGTGACGCAGC-CCCCGGZGGGATTGATCGGT-GGACACGGTGGCTGAC-3' |
| Z23-A30 SEQ ID NO. 9 | 5'-Biotin-TCCCGAGTGACGCAGC-CCCCGGZGGGATTAATCGGT-GGACACGGTGGCTGAC-3' |
| C23-P30 SEQ ID NO. 10 | 5'-Biotin-TCCCGAGTGACGCAGC-CCCCGGCGGGATTPATCGGT-GGACACGGTGGCTGAC-3' |
| T23-P30 SEQ ID NO. 11 | 5'-Biotin-TCCCGAGTGACGCAGC-CCCCGGTGGGATTPATCGGT-GGACACGGTGGCTGAC-3' |
| C23-G30 SEQ ID NO. 12 | 5'-Biotin-TCCCGAGTGACGCAGC-CCCCGGCGGGATTGATCGGT-GGACACGGTGGCTGAC-3' |
| T23-A30 SEQ ID NO. 13 | 5'-Biotin-TCCCGAGTGACGCAGC-CCCCGGTGGGATTAATCGGT-GGACACGGTGGCTGAC-3' |
| C23-A30 SEQ ID NO. 14 | 5'-Biotin-TCCCGAGTGACGCAGC-CCCCGGCGGGATTAATCGGT-GGACACGGTGGCTGAC-3' |
| T23-G30 SEQ ID NO. 15 | 5'-Biotin-TCCCGAGTGACGCAGC-CCCCGGTGGGATTGATCGGT-GGACACGGTGGCTGAC-3' |

Screening of Potential Aptamer Candidates.

Analysis of the Ion Torrent sequencing identified several other candidate aptamers with different arrangements of dZ and dP as well as those containing only normal bases. Each sequence was chemically synthesized and labeled with biotin at the 5' end. They were purified by HPLC (for IDT-derived oligos) or PAGE (for oligos prepared in house). These were quantified (UV 260/280) and diluted to standard concentrations.

Flow cytometry binding assays were then done using the target MDA-MB-231 cells. To obtain suspended cells for flow cytometry, culture medium was removed from the cells and non-enzymatic dissociation buffer was added to cover the surface of the entire flask. This was placed in an incubator at 37° C.

After incubation (5 min), the cells were aspirated using a transfer pipette to remove them from the flask. This was washed twice by centrifugation and approximately $5.0 \times 10^5$ cells were incubated separately with the aptamer candidates at a final concentration of 250 nM. After incubation, cells were washed. Streptavidin-PE-cy5.5 conjugate (100 µL of 1:400 dilution, optimized) was then added, and the mixture was incubated at 4° C. for 10 min. Excess dye conjugates were removed by washing twice and the cell-DNA complexes resuspended in 150 µL binding buffer. The aptamer binding signal was detected using flow cytometry (BD). Unselected library was used as a control to set the fluorescence background.

Determination of Binding Affinity.

The binding affinity of the aptamer ZAP-2012 was done by flow cytometry using biotin-labeled aptamer, and similarly the signal was detected with streptavidin-PE-cy5.5 conjugate. MDA-MB-231 cells were dissociated using non-enzymatic dissociation buffer. Cells were washed and incubated with varying concentrations (0.1 nM-500 nM final concentration) of biotin-labeled aptamer in a 200 mL volume of binding buffer containing 10% FBS. After 20 min of incubation, cells were washed twice with washing buffer and then incubated with 100 mL of the conjugate dye (1:400 dilution). This was incubated for 10 min and then washed twice, each with 1300 mL of washing buffer. The cell pellets were resuspended in 200 mL washing buffer and analyzed by flow cytometry. The biotin-labeled unselected library was used as a negative control to determine the background binding. All binding assays were done in duplicate. The mean fluorescence intensity of the unselected library was subtracted from that of the corresponding aptamer with the target cells to determine the specific binding of the labeled aptamer.

Results

GACTZP Aptamer Selection Scheme and AEGIS-SELEX Progression.

This AEGIS-SELEX began with the solid-phase synthesis of a GACTZP DNA library having two primer binding sequences (16 nts each) flanking a 20 nt random region ($N_1N_2 \ldots N_{20}$). Each of the 20 randomized sites was synthesized to have all six (GACTZP) phosphoramidites in equal amounts. In subsequent analysis, the library was digested and the nucleotide fragments were quantitated by HPLC to show that Z and P were present in the random region. The ratio of all six nucleotides was T/G/A/C/Z/P≈1.5/1.2/1.0/1.0/1.0/0.5.

A sample (5 nmol) of the GACTZP library was then subjected to sequential binding and elution from the line of breast cancer cells, MDA-MB-231. The pool of DNA survivors was collected after each round of selection and amplified by six-letter GACTZP PCR with a mixture of nucleotide triphosphates (dGTP, dATP, dCTP, dTTP, dZTP, and dPTP, Table S2) using Hot Start Taq DNA polymerase (TaKaRa). The product was recovered by binding to solid-phase streptavidin, followed by elution with NaOH. The resulting single stranded DNA was subjected to the next round of selection. No negative selection was used.

To increase the selection pressure in later rounds of AEGIS-SELEX, the number of cells and incubation times were gradually reduced, and the volume of washing buffer and the number of washes was increased. Starting after nine rounds of selection, the progress of the AEGIS-SELEX experiment was monitored by flow cytometry to measure the binding of the total library to the target cells. The amount of surviving GACTZP total DNA bound to MDA-MB-231 increased from $9^{th}$ round to $11^{th}$ round, but not further after 11th round. Therefore, the AEGIS-SELEX was stopped at 12th round, and the survivors were prepared for deep sequencing.

Deep Sequencing GACTZP DNA Survivors Using Next Generation Sequencing Technology.

Deep sequencing was done following the "conversion" strategy previously reported. The enriched GACTZP DNA survivors recovered after 12 rounds of AEGIS-SELEX were divided into two equal portions. These were separately converted by barcoded copying into standard DNA using two conversion protocols (Table S3). In the first protocol, sites holding Z and P nucleotides in the GACTZP survivors were converted predominantly into sites holding C and G nucleotides, respectively; less than 15% were other nucleotides. Under the second conversion protocol, sites holding Z were converted to sites holding a mixture of C and T, with their ratio lying between 60:40 and 40:60, depending on the sequence surrounding that site. Sites holding P is converted to a mixture of G and A with roughly the same range of ratios, again depending on the sequence context surrounding that site.

Following conversion, two barcoded samples were combined and submitted for Ion Torrent "next generation" sequencing at the University of Florida DNA sequencing Core facility (ICBR/UF). Reads that did not contain exactly matched barcodes and/or forward and reverse priming sequences were discarded. To minimize miscalling, any sequence present as fewer than 80 copies in the whole library was removed from the analysis. The remaining reads (357,574 in total) were then clustered using software custom designed at the FfAME, which ignored differing barcodes during the clustering and accepted single-step changes within sequence reads. Clustered sequences were then separated by barcode, with variable sites being compared between each barcode. The clustered sequences obtained under the first conversion conditions (Z to C and P to G) serve as reference for the clustered sequences obtained under the second conversion conditions. Sites where C and T were found in approximately equal amounts after conversion under the second conditions were assigned as Z in their "parent". Sites where G and A were found in approximately equal amounts after conversion under the second conditions were assigned as P in their "parent".

The inferred ancestral sequences were aligned to identify dominant candidate aptamers. One dominant aptamer sequence was represented by 101,224 independent reads, and constituted approximately 30% of the survivors. This aptamer was named ZAP-2012 (Z And P, 20 nucleotide random region, 12 cycles of selection), and its sequence was inferred to be: 5'-TCCCGAGTGACGCAGC-CCCCGG-ZGGGATTPATCGGT-GGACACGGTGGCTGAC-3'. SEQ ID NO. 16

ZAP-2012 contains a single Z at the position of 23 and a single P at the position of 30 (Z23-P30). The second and third most abundant sequences were about 5% and 3% of the population.

Determine the Binding Affinity of the Dominant Aptamer ZAP-2012 and Variants.

The ZAP-2012 aptamer was then re-synthesized in a form carrying a 5'-biotin by solid phase synthesis (ABI 394 DNA) from standard phosphoramidites (Glen Research) and dZ and dP phosphoramidites (Firebird Biomolecular Sciences LLC). Analogous molecules lacking Z (C23-P30 and T23-P30), lacking P (Z23-G30, Z23-A30), or lacking both Z and P (C23-G30, T23-G30, T23-A30, and C23-A30) were also synthesized with a 5'-biotin (Table S4).

These were each used at 250 nM in a flow cytometry assay (labeling with streptavidin-PE-Cy5.5) to test their binding to the MDA-MB-231 target cells. The original non-binding library was used as a negative control. The ZAP-2012 sequence bound strongly; its mutant forms gave either reduced binding (C23-P30, Z23-G30, and Z23-A30) or no binding at all (T23-P30, and all sequences lacking both Z and P). These studies illustrated that the Z and P nucleotides in ZAP-2012 significantly contribute to the binding affinity.

We also re-synthesized and tested the binding affinity of secondary survivors in the population, contributing from 5.0% to 0.4% of the total population of survivors. Among these twelve sequences, three had no Z and P; the remainder had either a single Z (and no P), a single P (and no Z), or one of each. Compared with the binding signal of the ZAP-2012, all twelve secondary candidates gave negligible binding signals. To rule out the mis-assignment of the Z and P in these candidates, we replaced Z by either C or T, and replace P by either G or A, to produce all possible fully standard sequence analogs, to exclude the possibility that these might be the "true" aptamer arising from the selection. Again, all these candidate sequences gave no binding signals at 250 nM. This shows that both Z and P are required for ZAP-2012 to bind.

Determination of Dissociation Constant of Aptamer ZAP-2012.

The dissociation constant ($K_{diss}$) of the ZAP-2012 aptamer against breast cancer cell (MDA-MB-231) was then estimated using serial dilutions (0.1 nM-500 nM final concentration). The biotin-labeled unselected library was used as a negative control to assess background binding. All binding assays were done in triplet. The mean fluorescence intensity of the unselected library was subtracted from that of the corresponding aptamer with the target cells to determine the specific binding of the labeled aptamer. The apparent $K_{diss}$ was obtained by fitting the intensity of binding versus the concentration of the aptamers to the equation $Y=B_{max}X/(K_{diss}+X)$; Y is the mean fluorescence intensity, at the concentration of aptamer=X in nanomoles; $B_{max}$ is maximal binding), using Sigma Plot (Jandel, San Rafael, Calif.). From these data, ZAP-2012 (Z23-P30) bound to the cell (MDA-MB-231) with an apparent $K_{diss}$=30±1 nM. If the Z in Z23-P30 is replaced by C to give C23-P30, the $K_{diss}$ increases to 160±31 nM. If the P in Z23-P30 is replaced by G to give Z23-G30, the $K_{diss}$ increases to 442±130 nM. All other mutant forms lacking Z (T23-P30), lacking P (Z23-A30), or lacking both Z and P (C23-G30, T23-A30, C23-A30, and T23-G30) gave almost no binding (the $K_{diss}$ increases to >1 µM).

What is claimed is:

1. A process for identifying one or more oligonucleotides that bind to a target, wherein at least one nucleobase of each of said one or more oligonucleotides has a structure selected from the group consisting of

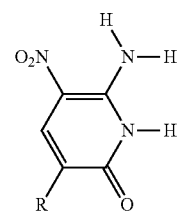 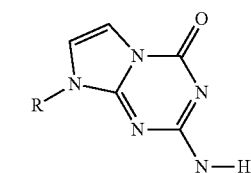

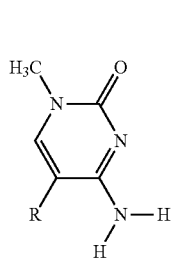 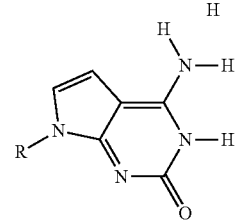 and

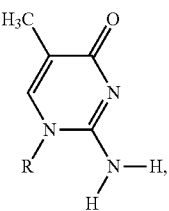

wherein R is the point of attachment of said nucleobase to said nucleotide, from a candidate mixture comprising single stranded oligonucleotides each having a region of randomized sequence, said process comprising:
a) contacting the candidate mixture with the target in aqueous solution.
b) separating the oligonucleotides having higher affinity for the target from oligonucleotides having lower affinity for the target;
c) amplifying the oligonucleotides having higher affinity for the target to yield a mixture enriched in said oligonucleotides having higher affinity, and
d) determining the sequence of one or more of said oligonucleotides, wherein said target is not a Watson-Crick complementary oligonucleotide.

2. The process of claim 1, wherein steps a), b), and c) are repeated multiple times on successively enriched mixtures.

3. The process of claim 1, wherein said nucleobase is

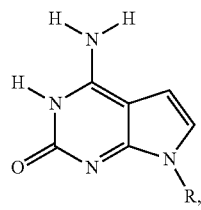

where R is the point of attachment of said nucleobase to the oligonucleotides at position 1' of the ribose or 2'-deoxyribose of said oligonucleotide.

4. The process of claim 1, wherein said nucleobase is

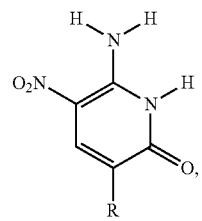

where R is the point of attachment of said nucleobase to the oligonucleotide at position 1' of the ribose or 2'-deoxyribose of said oligonucleotide.

5. The process of claim 1, wherein said nucleobase is

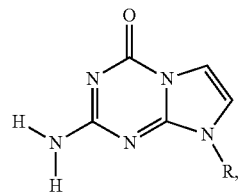

where R is the point of attachment of said nucleobase to the oligonucleotide at position 1' of the ribose or 2'-deoxyribose of said oligonucleotide.

6. The process of claim 1, wherein said nucleobase is

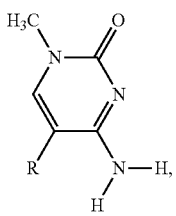

where R is the point of attachment of said nucleobase to the oligonucleotide at position 1' of the ribose or 2'-deoxyribose of said oligonucleotide.

7. The process of claim 1, wherein said nucleobase is

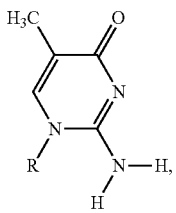

where R is the point of attachment of said nucleobase to the oligonucleotide at position 1' of the ribose or 2'-deoxyribose of said oligonucleotide.

8. The process of claim 1, wherein said nucleobase is

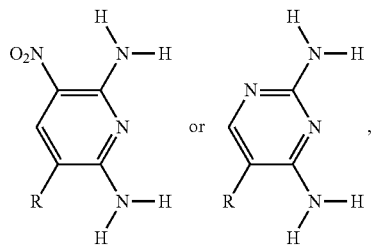

where R is the point of attachment of said nucleobase to the oligonucleotide at position 1' of the ribose or 2'-deoxyribose of said oligonucleotide.

9. The process of claim 1, wherein said nucleobase is

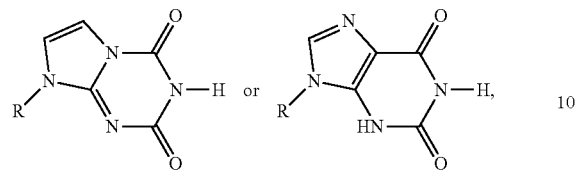

where R is the point of attachment of said nucleobase to the oligonucleotide at position 1' of the ribose or 2'-deoxyribose of said oligonucleotide.

10. The process of claim 1, wherein said target is on the surface of a cell.

11. The process of claim 1, wherein said target is a protein.

12. The process of claim 1, wherein said target is a small molecule.

* * * * *